United States Patent [19]

Bleha et al.

[11] 4,166,804

[45] Sep. 4, 1979

[54] POLYMERIC COLOR INDICATORS AND A METHOD OF THEIR PREPARATION

[75] Inventors: Miroslav Bleha; Zdeněk Plichta; Eva Votavová; Jaroslav Kálal, all of Prague, Czechoslovakia

[73] Assignee: Ceskoslovenska akademie ved, Prague, Czechoslovakia

[21] Appl. No.: 842,273

[22] Filed: Oct. 14, 1977

[30] Foreign Application Priority Data

Oct. 21, 1976 [CS] Czechoslovakia ............... 6778-76

[51] Int. Cl.² .................. G01N 21/08; C08J 9/00; C08F 8/30
[52] U.S. Cl. .................. 252/408; 23/230 R; 526/303; 526/320; 526/329; 526/329.7; 525/376
[58] Field of Search ............ 252/408; 23/253 TP, 23/230 R; 526/51, 50, 303, 320, 329, 329.7

[56] References Cited

U.S. PATENT DOCUMENTS

| | | |
|---|---|---|
| 2,732,382 | 1/1956 | Minsk et al. ............... 526/51 |
| 2,929,829 | 3/1960 | Morehouse ............... 252/408 |
| 3,544,484 | 12/1970 | Roth ............... 252/408 |
| 3,904,373 | 9/1975 | Harper ............... 23/253 TP |
| 3,925,267 | 12/1975 | Coupek et al. ............... 526/303 |
| 4,029,598 | 6/1977 | Neisius et al. ............... 252/408 |

FOREIGN PATENT DOCUMENTS 2436257 2/1976 Fed. Rep. of Germany ...... 23/253 TP
44-18580 8/1969 Japan ............... 526/51

Primary Examiner—Benjamin R. Padgett
Assistant Examiner—T. S. Gron

[57] ABSTRACT

Polymeric color pH indicators are prepared which are insoluble in the measured aqueous medium and show a certain range of color change. These polymeric indicators are the product of copolymerization of a hydrophilic comonomer, selected from esters, amides and N-substituted amides of acrylic and methacrylic acid, with 0.1–30 wt.% of a comonomer. The comonomer forms the pH-indicating color center by a subsequent coupling with a suitable diazonium salt or a passive component. Vinylic monomers comprising an aromatic system in the molecule are suitable as the functional comonomers. The indicators are prepared by radical copolymerization of the comonomers either in a suspension or in a solution, followed by the subsequent coupling with a diazonium compound, or diazotizing and coupling with a passive component, to obtain the pH-indicating sites of polymer. The product is in the form of small spherical macroporous particles suitable for pH indication in flow-through column processes, in small volumes, or on a microscope stage, or in the form of a solution applicable as a paint and indicating the pH of vessels, reactors, etc. coated therewith, or useful for application to inert carriers.

9 Claims, No Drawings

POLYMERIC COLOR INDICATORS AND A METHOD OF THEIR PREPARATION

The invention relates to polymeric color pH indicators, which are insoluble in the measured medium, which indicators have a certain range of color change, and also relates to a method of their preparation.

The acidobasic indicators used till now are soluble in water or organic solvents and possess a reversible function for indication of the change in hydrogen ion concentration. Organic dyes are mostly used which respond to the change of pH value by the change of their color. Soluble indicators become a part of the measured medium and cannot be used repeatedly in spite of their reversible function. The known "insoluble" indicators prepared by sorption of suitable compounds on a carrier (indicator papers) work in a broad region of pH scale, and very often cover the whole range of pH. When using this type of indicators, the extraction of dyes into the measured solution and also effect of the carrier (i.e. mostly of paper) on the measured pH value in small volumes of solutions cannot be excluded. For some types of indication, e.g. in flow-through column systems with a pH gradient, these kinds of indicators cannot be employed.

Other types of insoluble pH indicators are preparations made from soluble indicators chemically bonded on an insoluble carrier, e.g. on various forms of cellulose - foils, granules, etc.

The insoluble indicators, called also "nonextractible indicators", find their application in processes where pH needs to be determined without deterioration of the measured medium.

This occurs in numerous processes employed in the food industry, e.g. in dairy plants; in the photographic industry, e.g. for checking of baths, and the like. Also a continuous measurement of pH in flowing media in column processes is achieved by the fixation of insoluble pH indicators at suitable sites, as for example at pipe sight glasses, filters, etc. These indicators allow determination of pH at sites which are accessible only with difficulty, on a solid surface after its wetting, and the like.

The invention relates to polymeric color pH indicators, insoluble in the measured aqueous medium and having a certain range of color change, said indicators consisting of a comonomer, selected from the group comprising esters, amides, and N-substituted amides of acrylic and methacrylic acid, and of 0.1–30 wt.%, preferably 0.5–20 wt.%, of the monomer derived from acrylic or merhacrylic acid, which forms the pH indicating color center by the subsequent coupling reaction with a diazonium salt or with a passive component.

These polymeric color pH indicators according to this invention are prepared by the radical polymerization of corresponding comonomers and monomers and the coupling reaction of the resulting polymer in the form of small particles or solution with a diazonium salt or a passive coupling component giving rise to the color pH-indicating center.

As diazonium salts according to this invention, we include the diazotized aromatic amines, namely aniline and its carboxy, sulfo, hydroxy and amino derivatives, $\beta$-naphthylamine, $\alpha$-naphthylamine and their hydroxy, sulfo, carboxy and amino derivatives, aminoanthraquinone and its derivatives, and the like.

As a passive coupling component according to the invention, we employ aromatic compounds of the phenol derivative type, $\alpha$- and $\beta$-naphthols and their sulfo or amino and hydroxy derivatives, derivatives of 1-methyl-3-phenyl-5-pyrazolone, amino derivatives of naphthalene, and the like.

The aforesaid indicators are prepared by polymerization or copolymerization of suitable monomers, preferably of hydrophilic monomers, with addition of other comonomers, which enable the preparation of the indicating center by the polymer analogous reaction. Suitable monomers have to be chosen according to the type of application of the resulting indicator. Among the suitable ones may be named methacrylic and acrylic esters, amides, N-substituted amides, and the like. As esters of acrylic and methacrylic acid according to the invention, we employ esters of methacrylic and acrylic acid of hydrophilic nature, e.g. esters of ethylene glycol. As amides and substituted amides according to the invention, we employ methacrylamide, acrylamide, or N-substituted methyl, ethyl, and hydroxypropyl derivatives. The functional comonomers are mostly the monomers containing an aromatic system suitable as a passive component in the coupling reaction.

The polymers prepared in this way are then reacted with the diazonium salt of a suitable compound forming compounds, which are able to indicate pH in the range 1–12. We may also practice the procedure leading to preparation of the polymeric diazonium salt, and analogous materials may be prepared by the subsequent coupling with a suitable passive component.

Such copolymers may be advantageously prepared by a suspension copolymerization in the form of small spherical particles of porous character, which are suitable as column packings for pH indication in soiled, turbid or suspension systems. Single particles may be also employed for pH determinations in small volumes or in microscopic measurements. Another form of application and preparation is the synthesis of polymers as solutions which, applied as a paint on a suitable base, form the indicating film coat. Visual pH indicators made by application of this paint to walls of vessels, china rods, or to a suitable inert carrier (paper, textile). A universal pH indicator for certain pH region with the covalently bound indicating centers may be prepared by combination of a series of polymeric indicators.

The invention is further illustrated in the following examples without limiting its scope in any way.

EXAMPLE 1

The color polymeric indicator was prepared by a heterogeneous suspension polymerization of mixture of monomers consisting of 45.7 g of 2-hydroxyethyl methacrylate, 31.9 g of ethylene dimethacrylate, and 4.1 g of N-ethyl-N-(2-methacryloylethyl)aniline. The polymerization was initiated by 1% of azo-bis-isobutyronitrile and carried out in 600 g of water containing 6 g of polyvinylpyrrolidone with addition of 98.5 g cyclohexanol and 9.7 g of dodecanol at the temperature 60° C. for 15 hours. The resulting product contained 5% of the functional monomer and had a porous character with a specific surface area 63 m$^2$/g. The basic material prepared in this way was repeatedly extracted with water and ethanol. Spherical particles of the gel of diameter 50–100 $\mu$m (10 ml) were suspended in 50 ml of 20% acetic acid and 0.5 g of diazotized sulfanilic acid was added. The coupling reaction was carried out for 3 hours with stirring at the temperature 0° C. The obtained product of wine-red color may be used as the color pH indicator in the following range of values: pH=2.1—wine red; pH 2.6—red; pH=3.2—orange; pH=3.8—yellow.

EXAMPLE 2

The basic copolymer prepared according to Example 1 was coupled with benzenediazonium chloride in solution in the presence of pyridine. The prepared product may be used after washing as the color indicator for the following pH region: red—1.5, orange—1.9, yellow—2.9.

EXAMPLE 3

The basic copolymer prepared in Example 1 was mixed in an ethanol medium with a solution of diazotized anthranilic acid neutralized to pH 5. After 5 hours of reaction at 0° C., the resulting indicator was washed and showed the following pH values of color changes: red—5.3, orange—6.5, yellow—7.4.

EXAMPLE 4

The mixture of 0.6 g of 2-hydroxyethyl methacrylate and 0.03 g of N-ethyl-N-(2-methacryloylethyl)aniline was polymerized in a solution of 2.4 g methoxyethanol in the presence of 0.005 g of 2,2'-azo-bis-isobutyronitrile at 50° C. for 10 hours. The resulting viscous solution was diluted with 10 ml of 20% acetic acid, 0.1 g of diazotized sulfanilic acid was added at 5° C., and the mixture was stirred at this temperature for 1 hour. The resulting polymeric indicator was precipitated into 300 ml of water containing 20 g NaCl. After refining, the polymer was dissolved in 7 ml of 2-methoxyethanol and used for painting of arbitrary articles. The film of paint indicated on such articles changes of pH the region 2.1–3.8

EXAMPLE 5

The polymer solution prepared according to Example 4 was diluted with 10 ml ethanol and mixed with a solution of diazotized anthranilic acid neutralized by pyridine to pH 5. After 2 hours of reaction at 0° C., the resulting polymeric indicator was precipitated into a tenfold volume of NaCL solution and after refining dissolved in 2-methoxyethanol. Polymeric films prepared from this solution on china rods showed color changes with pH values in the region 5.3–7.4.

EXAMPLE 6

The polymeric indicators prepared according to Examples 1–3 were placed in the bottom of a flow-through column in successional layers 0.5 mm high. The obtained indication column enabled to measure continuously pH changes in the flow-through column in the region of pH 1.5–7.4.

EXAMPLE 7

The polymeric indicators prepared in a soluble form analogously to Examples 4 and 5 were used as an indication paint on a reactor. The polymeric coat obtained in this way allowed continuous measurement of pH in the region 1.5–7.4 pH.

Example 8

The polymeric color indicator was prepared by a heterogeneous polymerization of the monomer mixture consisting of 49.9 g of 2-hydroxyethyl methacrylate, 31.9 g of ethylene dimethacrylate and 1 g of N-ethyl-N-(2-methacryloylethyl)-N'-acetyl-p-phenylenediamine. The polymerization was initiated with 1% of azo-bis-isobutyronitrile and carried out in 600 g of water containing 6 g of polyvinylpyrrolidone with addition of 98.5 g of cyclohexanol and 9.7 g of dodecanol at the temperature 60° C. for 15 hours. The resulting product contained 1% of functional groups and had a macroporous character and a specific surface area 61 m$^2$/g. The prepared polymer was extracted and then diazotized at −5° C. under vigorous stirring and gradual addition of NaNo$_2$ in excess. After washing with aqueous solution and ethanol to disappearance of the reaction with NaNO$_2$, the polymer was dried and stored at +5° C. This material (1 g) was coupled in the medium of 0.2 N Na$_2$ CO$_3$ with 1-methyl-3-phenyl-5-pyrazolonsulfonic acid giving a pH indicator showing values in the pH region 10.2–11.9.

We claim:

1. Polymeric color changing pH indicators insoluble in aqueous medium when used for pH measurement thereof, said indicators being prepared by free radical polymerization of at least one comonomer selected from the group consisting of acrylic esters, methacrylic esters, acrylamide, methacrylamide, N-methylacrylamide, N-methylmethacrylamide, N-ethylacrylamide, N-ethylmethacrylamide, N-hydroxypropylmethacrylamide, and N-hydroxypropylmethylacrylamide, with from 0.1 to 30 weight percent of a functional monomer selected from the group consisting of N-ethyl-N-(2-methacryloyl) aniline and N-ethyl-N-(2-methacryloylethyl)-N'-acetyl-p-phenylenediamine to form a polymer, subsequently diazo-coupling said polymer with an aromatic active agent through the available functional sites of said monomer and functionally active sites of said agent. to set a pH color indicating center in said polymer.

2. Polymeric color changing pH indicators according to claim 1 wherein said active agent comprises a diazotized aromatic amine and said functional monomer is N-ethyl-N-(2-methylcryloylethyl) aniline.

3. Polymeric color changing pH indicators according to claim 2 wherein said aromatic amine is selected from the group consisting of aniline and its carboxy, sulfo, hydroxy, and amino derivatives; β-naphthylamine, α-naphthylamine, and their sulfo, carboxy, and amino derivatives; aminoanthraquinone and derivatives thereof.

4. Polymeric color changing pH indicators according to claim 1 wherein said active agent is selected from the group consisting of phenol derivatives; α-and β-naphthols and their sulfo or amino and hydroxy derivatives; derivatives of 1-methyl-3-phenyl-5-pyrazolon; and amino derivatives of naphthalene; said functional monmer is nethyl-N-(2-methacryloylethyl)-N'-acetyl-p-phenylenediamine, and said polymer is diazotized.

5. Method for preparing polymeric color changing pH indicators insoluble in aqueous medium when used for pH measurement comprising the steps of free radical polymerizing at least one comonomer selected from the group consisting of acrylic esters, methacrylic esters, acrylamide, methacrylamide, N-methylacrylamide, N-methylmethacrylamide, N-ethylacrylamide, N-ethylemelhacrylamide, N-hydroxypropylacrylamide, and N-hydroxypropylmethacrylamide, with from 0.1 to 30 weight percent of a functional monomer selected from the group, consisting of N-ethyl-N-(2-methacryloylethyl) aniline and N-ethyl-N-(2-methacryloylethyl)-N-acetyl-phenylenediamine, to form a polymer, subsequently diazo coupling said polymer with an aromatic, active agent through the available functional sites of said monomer and functionally active sites of said agent to set a pH color indicating center in said polymer.

6. Method according to claim 5, wherein from 0.5 to 20 weight percent of the monomer is employed.

7. Method according to claim 5, wherein said active agent comprises a diazotized aromatic amine and said moner is N-ethyl-N-(2-methacryloylethyl) aniline.

8. Method according to claim 7, wherein said aromatic amine is selected from the group consisting of aniline and its carboxy, sulfo, hydroxy and amino derivatives, β-naphthylamine, α-naphthylamine, and their sulfo-carboxy and amino derivatives, and aminoanthraquinone and derivatives thereof.

9. Method according to claim 5 wherein said active agent is selected from the group consisting of phenol derivatives; α- and β-naphthols and their sulfo and amino and hydroxy derivatives; derivatives of 1-methyl-3-phenyl-5-pyrazalone, and amino derivatives of naphthalene; said functional monomer is N-ethyl-N-(2-methacryloylethyl)-N'-acetyl-p-phenylenediamine, and said polymer is diazotized.

* * * * *